United States Patent
Page et al.

(10) Patent No.: US 9,290,740 B2
(45) Date of Patent: Mar. 22, 2016

(54) USE OF BASIC FIBROBLAST GROWTH FACTOR IN THE DE-DIFFERENTIATION OF ANIMAL CONNECTIVE TISSUE CELLS

(75) Inventors: Raymond L. Page, Southbridge, MA (US); Tanja Dominko, Southbridge, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 244 days.

(21) Appl. No.: 12/921,128

(22) PCT Filed: Mar. 9, 2009

(86) PCT No.: PCT/US2009/001517
§ 371 (c)(1),
(2), (4) Date: Dec. 1, 2010

(87) PCT Pub. No.: WO2009/111087
PCT Pub. Date: Sep. 11, 2009

(65) Prior Publication Data
US 2011/0064786 A1    Mar. 17, 2011

Related U.S. Application Data

(60) Provisional application No. 61/068,518, filed on Mar. 7, 2008.

(51) Int. Cl.
| | |
|---|---|
| *A61K 9/70* | (2006.01) |
| *A61P 7/00* | (2006.01) |
| *A61P 35/00* | (2006.01) |
| *A61P 3/10* | (2006.01) |
| *A61P 25/28* | (2006.01) |
| *A61K 35/12* | (2015.01) |
| *A61P 1/16* | (2006.01) |
| *C12N 5/071* | (2010.01) |
| *C12N 5/077* | (2010.01) |
| *A61P 25/00* | (2006.01) |
| *A61P 19/08* | (2006.01) |
| *C12N 5/0775* | (2010.01) |

(52) U.S. Cl.
CPC .......... *C12N 5/0662* (2013.01); *C12N 2500/02* (2013.01); *C12N 2501/115* (2013.01); *C12N 2506/1307* (2013.01)

(58) Field of Classification Search
CPC ............... C12N 5/0662; C12N 2506/1307; C12N 2500/02; C12N 2501/115; C12N 5/0696; C12N 2506/02; C12N 5/0606; A61K 35/545
See application file for complete search history.

(56) References Cited

U.S. PATENT DOCUMENTS

| | | | |
|---|---|---|---|
| 6,610,540 | B1 | 8/2003 | Csete et al. |
| 8,257,947 | B2 | 9/2012 | Naughton et al. |
| 8,524,494 | B2 | 9/2013 | Naughton et al. |
| 8,530,415 | B2 | 9/2013 | Naughton et al. |
| 8,535,913 | B2 | 9/2013 | Naughton et al. |
| 2001/0005592 | A1 | 6/2001 | Bhatnagar et al. |
| 2004/0142861 | A1 | 7/2004 | Mansbridge |
| 2010/0166824 | A1 | 7/2010 | Naughton et al. |

FOREIGN PATENT DOCUMENTS

| | | |
|---|---|---|
| WO | WO 2008/116213 A | 9/2008 |
| WO | WO 2009/111087 A1 | 9/2009 |

OTHER PUBLICATIONS

Thomson et al. PNAS, 92:7844-7848 (Aug. 1995).*
NIH. Stem Cells: Scientific Progress and Future Research Directions, Department of Health and Human Services, Chapter 1, pp. 1-4, Jun. 2001.*
Collas et al. Reproductive BioMedicine Online: 762-770, 2006.*
Oliveri et al. Regenerative Medicine, 2(5): 795-816, Sep. 2007.*
Sullivan et al. Reproductive BioMed. Online, 16(1): 41-50, Nov. 2008.*
Djuric and Ellis, 202, Stem Cell Research and Therapy, 2010,1:3.*
Takahashi, Cell, 2006, 126:663-676.*
Plath et al. Nature Reviews, 12: 253-265, 2011.*
Hochedlinger et al. Cell, 121: 465-477, May 6, 2005.*
Monk and Holding. Oncogene, 20: 8085-8091, 2001.*
Tsukada et al. In Vitro Cell Dev. Biol., 41:83-88, 2006.*
Coutu et al., Aging, 3(10): 920-933, 2011.*
Gospodarowicz et al., J. of Cell Biology, 66: 451-457, 1975.*
Imaizumi et al., J. of Dermatological Science, 11: 134-141, 1996.*
Talbot et al., Cloning & Stem Cells, 6(1): 37-47, 2004.*
Written Opinion for Int'l Application No. PCT/US2009/001517; Date Mailed: Aug. 14, 2009.
Notification Concerning Transmittal of International Preliminary Report on Patentability for Int'l Application No. PCT/US2009/001517; Date Mailed: Sep. 16, 2010.
Akita, S. et al., "The Quality of Pediatric Burn Scars is Improved by Early Administration of Basic Fibroblast Growth Factor," The *Journal of Burn Care & Research*, 27(3): 333-8 (2006).
Berg, Jonathan S. et al., "An Argument against a Role for Oct4 in Somatic Stem Cells," *Cell Stem Cell*, 1(4): 359-360 (2007).
Betts, Dean H. et al., "Low Oxygen Delays Fibroblast Senescence Despite Shorter Telomeres," *Biogentrology*, 9(1): 19-31 (2008).
Bushdid, P. B et al., "NF-κB Mediates FGF Signal Regulation of msx-1 Expression," *Devevelopmental Biology*, 237(1): 107-15 (2001).

(Continued)

*Primary Examiner* — Thaian N Ton
(74) *Attorney, Agent, or Firm* — Hamilton, Brook, Smith & Reynolds, P.C.

(57) ABSTRACT

De-differentiation protocols are described herein for generating progenitor cells from adult connective tissue, in particular adult human fibroblasts. The de-differentiation protocols described herein comprise culturing the differentiated cells with an amount of FGF2 to de-differentiate the cells. These de-differentiated cells may then be cultured and used for experimentation, amplification and clinical applications. The clinical applications include the use of the cells for tissue and cell based therapies.

17 Claims, 7 Drawing Sheets

(56) References Cited

OTHER PUBLICATIONS

Chakravarthy, M. V. et al., "Culture in Low Levels of Oxygen Enhances in vitro Proliferation Potential of Satellite Cells from Old Skeletal Muscles," *Cellular and Molecular Life Sciences*, 58(8): 1150-8 (2001).

Chen, H. L. at al., "Oxygen Tension Regulates Survival and Fate of Mouse Central Nervous System Precursors at Multiple Levels," *Stem Cells*, 25(9): 2291-301 (2007).

Cipolleschi, M. G. et al., "Severe Hypoxia Enhances the Formation of Erythroid Bursts from Human Cord Blood Cells and the Maintenance of BFU-E in vitro," *Experimental Hematology*, 25(11): 1187-94 (1997).

Csete, M. et al., "Oxygen-Mediated Regulation of Skeletal Muscle Satellite Cell Proliferation and Adipogenesis in Culture," *Journal of Cellular Physiology*, 189(2): 189-96 (2001).

Didinsky, J.B, and Rheinhold, J.G., "Failure of Hydrocortizone or Growth Factors to Influence the Senescence of Fibroblasts in a New Culture System for Assessing Replicative Lifespan," *Journal of Cellular Physiology*, 109(2): 171-179 (1981).

Ezashi, T., et al., "Low O2 Tensions and the Prevention of Differentiation of hES cells," *PNAS USA*, 102(13): 4783-8 (2005).

Fink, T., L. Abildtrup, et al., "Induction of Adipocyte-Like Phenotype in Human Mesenchymal Stem Cells by Hypoxia," *Stem Cells* 22(7): 1346-55 (2004).

Fischer, A. J. and T. A. Reh, "Exogenous Growth Factors Stimulate the Regeneration of Ganglion Cells in the Chicken Retina," *Developmental Biology*, 251(2): 367-79 (2002).

Forsyth, N. R. et al., "Physiologic Oxygen Enhances Human Embryonic Stem Cell Clonal Recovery and Reduces Chromosomal Abnormalities," *Cloning Stern Cells*, 8(1): 16-23 (2006).

Grayson, W. L. et al., "Hypoxia Enhances Proliferation and Tissue Formation of Human Mesenchymal Stem Cells," *Biochemical and Biophysical Research* Communications, 358(3): 948-53 (2007).

Grayson, W. L. et al., "Effects of Hypoxia on Human Mesenchymal Stem Cell Expansion and Plasticity in 3D Constructs," *Journal of Cellular Physiology*, 207(2): 331-9 (2006).

Hayashi, T. et aL, "FGF2 Triggers Iris-Derived Lens Regeneration in Newt Eye," *Mechanisms of Development*, 121(6): 519-26 (2004).

Hung, S. C. et al., "Short-Term Exposure of Multipotent Stromal Cells to Low Oxygen Increases their Expression of CX3CR1 and CXCR4 and their Engraftment in vivo," *PLoS ONE*, 2(5): e416 (2007).

Ivanovic, Z., B. Bartolozzi, et al., "Incubation of Murine Bone Marrow Cells in Hypoxia Ensures the Maintenance of Marrow-Repopulating Ability Together with the Expansion of Committed Progenitors," *British Journal of Haematology*, 108(2): 424-9 (2000).

Ivanovic, Z., et al., "Primitive Human HPCs are Better Maintained and Expanded in vitro at 1 percent Oxygen than at 20 percent," *Transfusion*, 40(12): 1482-8 (2000).

Ivanovic, Z., et al., "Simultaneous Maintenance of Human Cord Blood SCID-Repopulating Cells and Expansion of Committed Progenitors at Low O2 Concentration (3%)," *Stem Cells*, 22(5): 716-24 (2004).

Jeong, C. H., et al., "Hypoxia-Inducible Factor-1α Inhibits Self-Renewal of Mouse Embryonic Stem Cells in vitro via Negative Regulation of the Leukemia Inhibitory Factor-STAT3 Pathway," *Journal of Biological Chemistry*, 282(18): 13672-9 (2007).

Kimelman, D., "The Presence of Fibroblast Growth Factor in the Frog Egg: Its Role as a Natural Mesodeisn Inducer," *Science*, 242(4881): 1053-6 (1988).

Knee, R. S. et al., "Basic Fibroblast Growth Factor Sense (FGF) and Antisense (gfg) RNA Transcripts are Expressed in Unfertilized Human Oocytes and in Differentiated Adult Tissues," *Biochemical and Biophysical Researach Communicationsi*, 205(1): 577-83 (1994).

Kondo, H. and Y. Yonezawa, "Fetal-Adult Phenotype Transition, in Terms of the Serum Dependency and Growth Factor Requirements, of Human Skin Fibroblast Migration," *Exp Cell Res* 220(2): 501-4 (1995).

Kostakopoulou, K. et al., "Regeneration' of Wing Bud Stumps of Chick Embryos and Reactivation of Msx-1 and Shh Expression in Response to FGF-4 and Ridge Signals," Mechanisms of Development, 55(2): 119-31 (1996).

Murphy, P. R. and R. S. Knee, "Identification and Characterization of an Antisense RNA Transcript (gfg) from the Human Basic Fibroblast Growth Factor Gene," *Molecular Endocrinology*, 8(7): 852-9 (1994).

Nakagawa, H. et al., "Human Mesenchymal Stem Cells Successfully Improve Skin-Substitute Wound Healing," *The British Journal of Dermatology*, 153(1): 29-36 (2005).

Nakagawa, M. et al., "Generation of Induced Pluripotent Stem Cells without Myc from Mouse and Human Fibroblasts," *Nature Biotechnologyl*, 26(1): 101-106 (2008).

Packer, L. and K. Fuehr, "Low Oxygen Concentration Extends the Lifespan of Cultured Human Diploid Cells," *Nature*, 267(5610): 423-5 (1977).

Parrinello, S. et al., "Oxygen Sensitivity Severely Limits the Replicative Lifespan of Murine Fibroblasts," *Nature Cell Biology*, 5(8): 741-7 (2003).

Pistollato, F. et al., "Oxygen Tension Controls the Expansion of Human CNS Precursors and the Generation of Astrocytes and Oligodendrocytes," *Mol Cell Neurosci* 35(3): 424-35 (2007).

Saito, H. et al., "The Effect of Low Oxygen Tension on the in Vitro-Replicative Life Span of Human Diploid Fibroblast Cells and Their Transformed Derivatives," *Experimental Cell Research*, 217(2): 272-279 (1995).

Sakaguchi, D. S. et al., "Basic Fibroblast Growth Factor (FGF-2) Induced Transdifferentiation of Retinal Pigment Epithelium: Generation of Retinal Neurons and Glia," *Developmental Dynamics*, 209(4): 387-98 (1997).

Takahashi, K. et al., "Induction of Pluripotent Stem Cells from Fibroblast Cultures," *Nature Protocols*, 2(12): 3081-9 (2007).

Wang, D. W. et al., "Influence of Oxygen on the Proliferation and Metabolism of Adipose Derived Adult Stem Cells," *Journal of Cellular Physiology*, 204(1): 184-91 (2005).

Yu, J. et al., "Induced Pluripotent Stem Cell Lines Derived from Human Somatic Cells," *Science*, 318(5858): 1917-20 (2007).

Zenjari, C. et al., "Nerve-Blastema Interactions Induce Fibroblast Growth Factor-1 Release During Limb Regeneration in Pleurodeles waltl," *Dev. Growth Differ.*, 39(1): 15-22 (1997).

International Search Report for PCT/US2009/001517 mailed Aug. 14, 2009.

Street, et al., "Hypoxia Regulates The Paracrine Coupling Of Angiogenesis and Bone Formation," *Eur. J. Orthop. Surg. Traumatol.*, 2005, vol. 15, pp. 214-225.

Siddiqui, et al., "Differential Effects of Oxygen on Human Dermal Fibro-Blasts: Acute Versus Chronic Hypoxia," *Wound Repair and Regeneration*, 1996, vol. 4, pp. 211-218.

King-Briggs, Kathryn E. and Shanahan, Catherine M., "TGF-β superfamily members do not promote smooth muscle-specific alternative splicing, a late marker of vascular smooth muscle cell differentiation," *Differentiation*, 2000, vol. 66, pp. 43-48.

Brazel, Christine Y. et al., "Sox2 expression defines a heterogeneous population of neurosphere-forming cells in the adult murine brain," *Aging Cell*, 2005, vol. 4, pp. 197-207.

Casimer, C.M., et al., "Evidence for Dedifferentiation and Metaplasia in Amphibian Limb Regeneration From Inheritance of DNA Methylation," Development, 104: 657-668 (1988).

Jez, M., et al., "Expression and Differentiation Between OCT4A and Its Pseudogenes in Human ESCs and Differentiated Adult Somatic Cells," PLOS One 9(2): e89546, 1-10 (Feb. 2014).

Koning, M., et al., "Hypoxia Promotes Proliferation of Human Myogenic Satellite Cells: A Potential Benefactor of Tissue Engineering of Skeletal Muscle," Tissue Engineering, p. A, 17(13 and 14): 1747-1758 (2010).

(56) References Cited

OTHER PUBLICATIONS

Page, R.L., et al., "Induction of Stem Cell Gene Expression in Adult Human Fibroblasts Without Transgenes," Cloning and Stem Cells, 11(3): 1-8 (2009).

Schnabel, M., et al., "Dedifferentiation-Associated Changes in Morphology and Gene Expression in Primary Human Articular Chondrocytes in Cell Culture," Osteoarthritis and Cartilage, 10: 62-70 (2002).

Siggiqui, A., et al., "Differential Effects of Oxygen on Human Dermal Fibroblasts: Acute Versus Chronic Hypoxia," Wound Repair and Regeneration, 211-218 (Apr.-Jun. 1996).

Slocum, D.L., "Amphibian Regeneration and Stem Cells," Current Topics in Microbiology and Immunology, 280: 1-70 (2004).

Street, J.T., et al., "Hypoxia Regulates the Paracrine Coupling of Angiogenesis and Bone Formation," Eur. J. Orthop. Surg. Traumatol., 15: 214-225 (2005).

\* cited by examiner

USE OF BASIC FIBROBLAST GROWTH FACTOR IN THE DE-DIFFERENTIATION OF ANIMAL CONNECTIVE TISSUE CELLS

RELATED APPLICATION

This application is the U.S. National Stage of International Application No. PCT/US2009/001517, filed Mar. 9, 2009, which designates the U.S., published in English, and claims the benefit of U.S. Provisional Application No. 61/068,518, filed on Mar. 7, 2008, the entire teachings of which are incorporated herein by reference.

GOVERNMENT SUPPORT

The invention was supported, in whole or in part, by contract number W911NF-06-1-0161 from U.S. Army RDECOM ACQ CTR-W911NF. The Government has certain rights in the invention.

BACKGROUND OF THE INVENTION

De-differentiation protocols are useful for creating pluripotent cells from adult connective tissue for experimentation, amplification and clinical applications. Current de-differentiation protocols to achieve pluripotent cells are inefficient and limited. Furthermore, the use of growth factors and manipulation of culture conditions have been utilized to increase proliferation rates of cell cultures with limited success.

Typically, in culturing fibroblasts, primary fibroblasts are used. One major limitation in using primary cells for the study of disease is their limited in vitro lifespan and contributes to why primary adult derived human cell lines for are used infrequently in genetic research. During the process of DNA transfection, and subsequent cell amplification, primary cells reach their in vitro proliferation potential making extended studies impossible. Thus, a need exists for increasing the life span of cultured connective tissue for extended studies on successfully genetically modified cells.

Additionally, utilizing adult fibroblast and developing cultures specific to individuals or animals would be advantageous in clinical applications for these individuals. Thus, a need exists for generating de-differentiated connective tissue cells from an individual.

SUMMARY OF THE INVENTION

This invention provides methods for de-differentiation of animal connective tissue cells, in particular fibroblasts. In one aspect, a method of culturing in the presence of growth factors, in particular, FGF2, for de-differentiation of animal connective tissue cells is described. In one aspect of the invention, a method for de-differentiation of tissue cells is described using FGF2 combined with culture conditions, for example, low oxygen culture for de-differentiation of animal culture cells. In another aspect, the culturing conditions further include culture medium comprising an extra-cellular matrix. In one aspect, the cells utilized in the methods of the invention are fibroblasts, for example, adult human dermal fibroblasts. In another aspect, the cells utilized in the methods of the invention are derived from animals, for example a mammal, such as a human, non-human, primate, mouse, rat, rabbit, horse, pig, cow, dog, cat, other companion animals.

Described herein are methods of generating cell cultures with increased longevity by use of the growth factor, FGF2 and low oxygen conditions. Such cultures are useful for experimentation, modeling and expansion of primary cells. In some embodiment, a two fold increase is observed. The therapeutic use of cells with increased life-span are advantageous for autologous transplantation for soft tissue injury such as dermal defects (burns), muscle injury, maxillofacial reconstruction.

In one aspect, a method of de-differentiating connective cells, comprising culturing the cells in a medium that comprises a fibroblast growth factor in an effective amount and under culturing conditions; thereby producing de-differentiated cells and expanding the de-differentiated cells is described. In certain aspects, the cells are adult animal fibroblasts, for example mammalian fibroblast, or example, adult human dermal fibroblasts. In certain embodiments, the fibroblast growth factor is basic fibroblast growth factor (FGF2), for example recombinant human FGF2. In certain aspects the concentration of FGF2 is a range between about 1 ng/ml to about 9 ng/ml, between about 2 ng/ml to about 8 ng/ml, 3 ng/ml to about 7 ng/ml, or about 4 ng/ml, 5 ng/ml or 6 ng/ml.

In certain other aspects, the culture conditions include low oxygen conditions such as about 1% to about 10%, and in certain embodiments about 5.0% oxygen. In other aspects, the culture conditions include as medium that comprises other growth factors, including but not limited to: Epidermal Growth Factor, Platelet Derived Growth Factor, Acidic Fibroblast Growth Factor, Transforming Growth Factor alpha, Transforming Growth Factor beta, Keratinocyte Growth Factor, Insulin, Insulin-Like Growth Factor 1 or 2, Tumor Necrosis Factor, FGF4 and combinations thereof.

The invention also pertains to a method of de-differentiating adult human fibroblasts, comprising culturing the fibroblasts under low oxygen conditions in a medium that comprises basic fibroblast growth factor in the presence of an extra-cellular matrix; and expanding the culture, wherein the expanded cells are induced de-differentiated cells. Also, the invention relates to a cell culture comprising de-differentiated fibroblast cells produced by treatment with FGF2 under low oxygen conditions. A method of de-differentiating adult fibroblasts comprising, culturing the fibroblasts with FGF2, wherein at least one stem cell transcription marker is expressed is also described. In certain aspects, the stem cell transcription marker is Msx-2, Sox-2, Oct-4, Nanog and combinations thereof.

In certain embodiments, an activated cell culture surface is included in the culture conditions. In certain aspects, the cell culture surface is a non-polystyrene surface. In other aspects, the cell culture surface is glass.

In one aspect, an activated cell culture surface and histone deacetylase inhibitor is included with FGF2 in the de-differentiation protocols described herein. In a particular embodiment, the histone deacetylase inhibitor is valproic acid. In particular embodiments, the activated cell surface is glass. In other aspects, a culture substrate is included, for example, MATRIGEL®. The amount of MATRIGEL® for optimal use can be determined. In certain embodiments, the amount is sub-optimal for cell attachment but not at a concentration where the cell do not grow. In certain aspects of the invention modulators of growth factors can also be included. In particular aspect, heparin sulfate is included as a modulator of FGF2.

The invention also pertains to a wound dressing, comprising: de-differentiated adult human fibroblasts, basic fibroblast growth factor and a delivery matrix. In certain aspects, the delivery matrix is a matrix that allows for the delivery of the cells to the wound site. In certain aspects, the wound dressing further comprises other growth factors. In a particular aspect, the other growth factors include FGF4.

The delivery matrix includes but is not limited to: gelatin, collagen, denatured collagen, glycine, poly-lysine, fibronectin, laminin, fibrinogen, and combinations thereof. The matrix can also include other materials that are known to provide a matrix for cell growth. The matrix can also include commercial culture substrates, for example MATRIGEL®.

FGF2, along with low oxygen culture and appropriate extracellular matrix play a role in the ability to create pluripotent cells from adult connective tissue cells. Adult stem cells exist (in vivo) in a critically defined environmental niche, likely maintained by a precise complement of growth factors and extracellular matrix. There is speculation about whether stem cells can be recruited from differentiated cells based on properties of the "stem cell niche." Described herein are methods of inducing a stem cell or blastema cell-like state in vitro from a differentiated cell and then "trapping" the cells in that state using specialized culture conditions. The resultant cells are then useful for further amplification and clinical applications. This is achieved by the inductive effect of FGF2 and other cell culture conditions as described herein.

The invention also pertains to methods of treating a disorder in an animal in need of tissue or cell therapy, comprising, administering to the animal de-differentiated cells wherein the de-differentiated cells are prepared from de-differentiating connective cells in a medium that comprises a fibroblast growth factor in an effective amount and under culturing conditions. Disorders include but are not limited to: heart diseases, strokes, diabetes, liver diseases, neurodegenerative diseases, cancers, tumors, spinal cord injury or diseases, brain diseases, skin diseases, bone diseases, blood diseases, Alzheimer's disease, Parkinson's disease, multiple sclerosis, amyotrophic lateral sclerosis (ALS), and disorders caused by single gene defects and the like.

The cells for use in these methods are prepared from de-differentiating connective cells in a medium that comprises a fibroblast growth factor in an effective amount and under culturing conditions, the culturing conditions include low oxygen conditions, for example about 5.0% oxygen. In certain methods, it is beneficial that the cells be from the animal in need of tissue or cell therapy. In certain aspects the cells are adult fibroblasts, for example, mammalian. In other aspects, the cell de-differentiation medium, further comprising an extra-cellular matrix.

The invention also pertains to methods of treating an animal in need of therapeutic progenitor cells, comprising: administering to the animal therapeutic progenitor cells, wherein the progenitor cells are prepared from de-differentiating connective cells in a medium that comprises a fibroblast growth factor in an effective amount and under culturing conditions. In certain methods, it is beneficial that the cells be from the animal in need of tissue or cell therapy. In certain aspects the cells are adult fibroblasts, for example, mammalian adult fibroblasts. In other aspects, the cell de-differentiation comprises a medium for use under culture conditions for the promotion of de-differentiation. In other aspects, the medium further includes an extra-cellular matrix.

Methods of de-differentiating connective cells, comprising culturing the cells in a medium that comprises a fibroblast growth factor (FGF2) in an effective amount, heparin sulfate in an effective amount, at least one HDAC inhibitor in an effective amount, in the presence of glass substrate and under culturing conditions comprising low oxygen (for example about 1% to about 10%) thereby producing de-differentiated cells and expanding the de-differentiated cells are also described. In certain embodiments, the method further includes growth factors, for example, insulin and insulin like growth factor.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
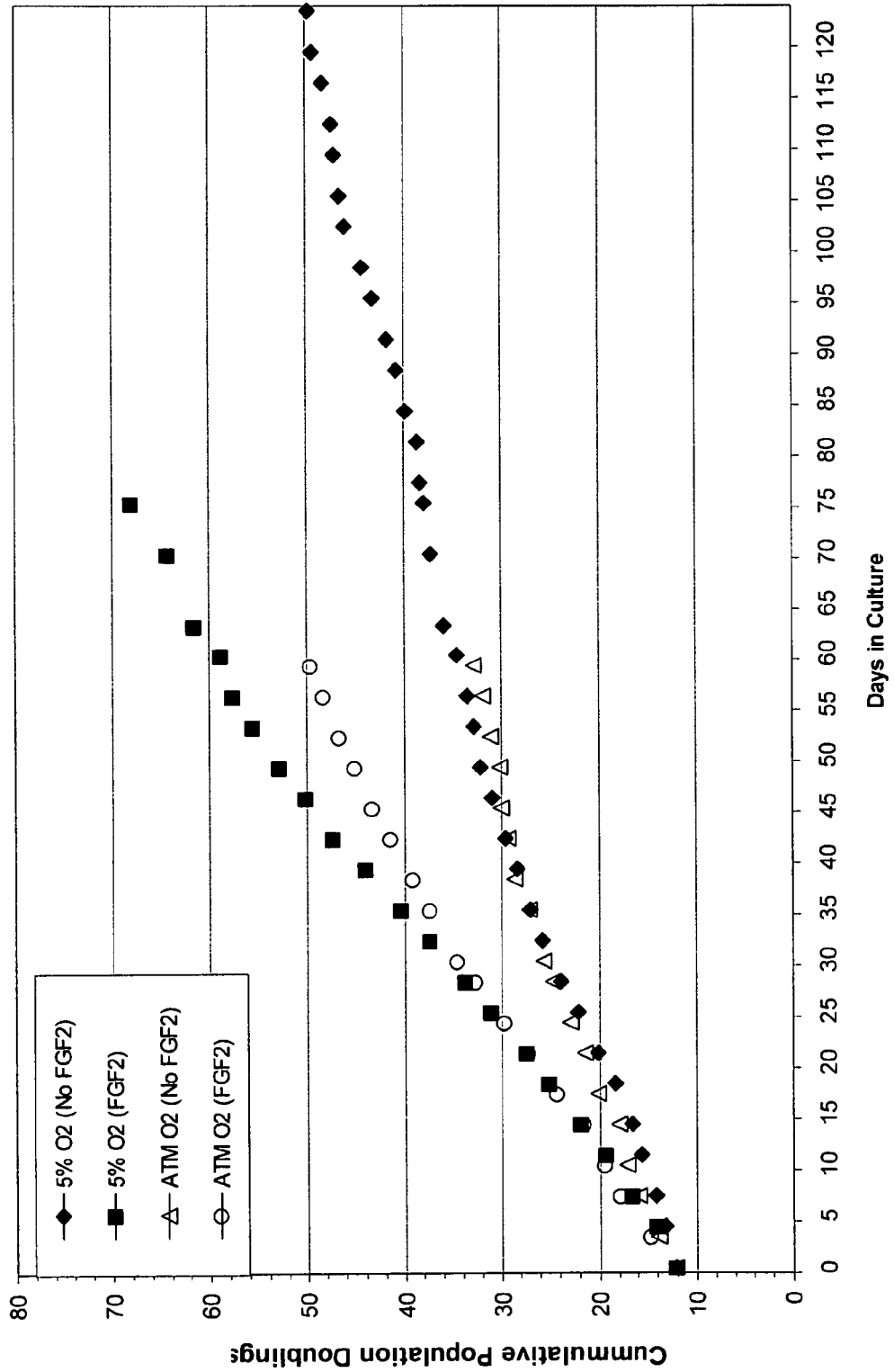
FIG. 1 is a graph showing the effect of FGF2 (4 ng/ml) on in vitro growth of adult human dermal fibroblasts (CRL-2352) compared with control. The average number of population doublings (PDs) at each passage (regular intervals and seed at the same density) and cumulative PDs plotted versus time (days) in culture.

A description of example embodiments of the invention follows.

Fibroblast Growth Factors (FGF's), especially FGF2, have been studied widely because of their ability to induce cell proliferation and migration, which has prompted many studies of FGF's effect in dermal wound healing.

FGF2's have been reported to alleviate the necessity of feeder cells for maintenance of an undifferentiated cell phenotype (in vitro). Studies show human embryonic stem cells grown in the absence of embryonic fibroblasts require FGF2 to remain undifferentiated. Recently, it has been shown that transfection of specific cocktails of factors into fibroblasts can induce pluripotency in both mouse cells (Takahashi, K., K. Okita et al., "Induction of Pluripotent Stem Cells from Fibroblast Cultures," *Nat Protoc*, 2(12): 3081-9 (2007)) and human cells (Nakagawa, M., M. Koyanagi et al., "Generation of Induced Pluripotent Stem Cells without Myc from Mouse and Human Fibroblasts," *Nat Biotechnol* (2007); Yu, J., M. A. Vodyanik et al., "Induced Pluripotent Stem Cell Lines Derived from Human Somatic Cells," *Science*, 318(5858): 1917-20 (2007)). Activation of Oct4, Sox2, Nanog and Lin28 appears to be sufficient to set in motion a cascade of molecular events leading to acquisition of pluripotency with characteristics of ESCs. In the human cells, the transcription factors Sox-2 and Oct-4 were absolutely required to achieve this transformation. While the addition of nanog was beneficial, nanog was not required to achieve pluripotency nor was it capable of inducing pluripotency on its own. Pluripotency was achieved by addition of the histone deacetylase inhibitor valproic acid along with only Oct4 and Sox2 expressing transgenes (Huangfu, D. et al. *Nat Biotechnol*, (2008)). These achievements have groundbreaking implications for embryonic stem cell research since cells with nearly equivalent differentiation potential can be created without using embryonic material or first obtaining embryos using somatic cell nuclear transfer. However, therapeutic applications may be limited due to the fact that these techniques require transgenic modification of the cells that increases the risk of mutagenic effects that may result in tumorigencity. While the literature regarding the specific effect of FGF2 on gene expression in adult human fibroblasts is minimal, there is data that demonstrates a marked difference in fibroblast migration due to grown factor induction between fetal and adult fibroblasts (Kondo, H. and Y. Yonezawa, "Fetal-Adult Phenotype Transition, in Terms of the Serum Dependency and Growth Factor Requirements, of Human Skin Fibroblast Migration," *Exp Cell Res*, 220(2): 501-4 (1995)). Specifically, fetal and neonatal fibroblasts are more migratory under the influence of FGF2, whereas adult fibroblasts are more responsive to PDGF. A morphogenic role for FGF2 in other cell types, particularly transdifferentiation of retinal pigmented epithelium has been suggested (Sakaguchi, D. S., L. M. Janick et al., "Basic Fibroblast Growth Factor (FGF-2); Induced Transdifferentiation of Retinal Pigment Epithelium: Generation of Retinal Neurons and Glia," *Dev Dyn*, 209(4): 387-98 (1997)) and regeneration of ganglion cells in chicken retina (Fischer, A. J. and T. A. Reh, "Exogenous Growth Factors Stimulate the Regeneration of Ganglion Cells in the Chicken Retina," *Dev Biol*, 251(2): 367-79 (2002)). Also, a recent clinical trial using FGF2 for treatment of pediatric burns demonstrated improved functional outcome due to exogenous FGF2 (Akita, S., K. Akino et al., "The Quality of Pediatric Burn Scars is Improved by Early Administration of Basic Fibroblast Growth Factor," *J Burn Care Res*, 27(3): 333-8 (2006)). Report of limb development studies in the chicken have shown an inductive response of Msx-1 due to FGF2 mediated through nuclear factor-kappaB (NF-kappaB) (Bushdid, P. B., C. L. Chen et al., "NF-kappaB Mediates FGF Signal Regulation of msx-1 Expression," *Dev Biol*, 237(1): 107-15 (2001)). In amputation/regeneration studies of the chick limb bud, FGF4 has been shown to lead to restoration through Msx-1 and Shh reactivation (Kostakopoulou, K., A. Vogel et al., "'Regeneration' of Wing Bud Stumps of Chick Embryos and Reactivation of Msx-1 and Shh Expression in Response to FGF-4 and Ridge Signals," *Mech Dev*, 55(2): 119-31 (1996)). FGF2 injected into the newt eye led to restoration of lens tissue due to induction of Pax6, Sox-2 and MafB (Hayashi, T., N. Mizuno et al., "FGF2 Triggers Iris-Derived Lens Regeneration in Newt Eye," *Mech Dev*, 121(6): 519-26 (2004)). U.S. Pat. No. 6,582,960 to Massachusetts Institute of Technology describes the use of FGF2 for expansion of chondrocytes and tissue engineering. The patent teaches a method of de-differentiating chrondrocytes by suspending differentiation. Thus, the cells are expanded in the presence of FGF2 at a specified stage and later differentiated and used in tissue engineering. The de-differentiation results in the cells no longer producing characteristic markers that define them as being differentiated, but are later subjected to conditions for differentiation.

Maintenance of inherent (ESC) or induced (iPS) pluripotency in human cells depends on continuous presence of FGF2 (Levenstein, M. E. et al., *Stem Cells*, 24, 568-74 (2006) as its withdrawal leads to spontaneous cell differentiation (Diecke, S., Quiroga-Negreira, A., Redmer, T. & Besser, D., Cells Tissues Organs 188, 52-61 (2008). FGF2 induced differential expression of members of the TGF-β family of proteins. Upregulation of TGF-β1, activin A (TGF-β receptor and ALK receptor ligand, respectively) and gremlin1 (BMP4 inhibitor), and downregulation of BMP4 led to SMAD2/3 driven expression of Oct4, Sox 2 and Nanog (Suzuki, A. et al., *PNAS USA* 103, 10294-9 (2006)). These three transcription factors co-occupy promoters of several genes, including FGF2. Increased expression of FGF2 completes this autoregulatory loop that is perpetuated in the presence of exogenous FGF2. Interestingly, a very similar effect of FGF2 on expression of the TGF-β family members was observed in fibroblasts used to support growth and maintenance of hESC (Greber, B., et al., *Stem Cells*, 15:455-464 (2007)). Reducing oxygen concentration during culture is becoming increasingly more appreciated in hESC laboratories (Ezashi, T et al., *PNAS USA*, 102, 4783-8 (2005)). Adult and embryonic stem cells cultured in a reduced oxygen atmosphere have been shown to both maintain their undifferentiated state more efficiently and increase the efficiency of their differentiation upon induction (Chakravarthy, M. V. et al., *Cell Mol Life Sci.*, 58, 1150-8 (2001); Covello, K. L. et al., *Genes Dev* 20, 557-70 (2006); Fink, T. et al., *Stem Cells*, 22, 1346-55 (2004); Forsyth, N. R et al. *Cloning Stem Cells* 8, 16-23 (2006); Grayson, W. L. et al., *Biochem Biophys Res Commun.*, 358, 948-53 (2007); Grayson, W. L., et al., *J Cell Physiol*, 207, 331-9 (2006); and Pistollato, F. et al., *Mol Cell Neurosci.*, 35, 424-35 (2007)).

Furthermore, despite evidence that low oxygen culture has a beneficial effect on growth potential of cells in vitro few researchers have adopted its use for studies of primary somatic cell cultures, particularly fibroblasts (Packer, L. and K. Fuehr, "Low Oxygen Concentration Extends the Lifespan of Cultured Human Diploid Cells," *Nature*, 267(5610): 423-5 (1977); Parrinello, S., E. Samper et al., "*Nat Cell Biol*, 5(8): 741-7 (2003)). Low oxygen culture has been gaining popularity with researchers culturing mesenchymal stem cells, embryonic stem cells and other adult stem cells (Cipolleschi, M. G., G. D'Ippolito et al., *Exp Hematol*, 25(11): 1187-94 (1997); Ivanovic, Z., B. Bartolozzi et al., *Br J Haematol*, 108(2): 424-9 (2000); Ivanovic, Z., P. Dello Sbarba et al, *Transfusion*, 40(12): 1482-8 (2000); Chakravarthy, M. V., E. E. Spangenburg et al., *Cell Mol Life Sci*, 58(8): 1150-8 (2001); Csete, M., J. Walikonis et al., *J Cell Physiol*, 189(2): 189-96 (2001); Fink, T., L. Abildtrup et al., *Stem Cells*, 22(7): 1346-55 (2004); Ivanovic, Z., F. Hermitte et al., *Stem Cells*, 22(5): 716-24 (2004); Ezashi, T., P. Das et al., *Proc Natl Acad Sci USA*, 102(13): 4783-8 (2005); Wang, D. W., B. Fermor et al, *J Cell Physiol*, 204(1): 184-91 (2005); Forsyth, N. R., A. Musio, et al., *Cloning Stem Cells*, 8(1): 16-23 (2006); Grayson, W. L., F. Zhao et al., *J Cell Physiol*, 207(2): 331-9 (2006); Chen, H. L., F. Pistollato et al., *Stem Cells*, 25(9): 2291-301 (2007); Grayson, W. L., F. Zhao et al., *Biochem Biophys Res Commun*, 358(3): 948-53 (2007); Hung, S. C., R. R. Pochampally et al., *PLoS ONE*, 2(5): e416 (2007); Jeong, C. H., H. J.

Lee et al., *J Biol Chem*, 282(18): 13672-9 (2007); Pistollato, F., H. L. Chen et al., *Mol Cell Neurosci*, 35(3): 424-35 (2007)).

Methods of culturing in the presence of growth factors for de-differentiation of animal connective tissue cells are described. In one aspect of the invention, a method for de-differentiation of tissue cells is described using FGF2. In another aspect of the invention, FGF2 is combined with culture conditions, for example, low oxygen culture for de-differentiation of animal culture cells. In other aspects, the invention further comprises the use of a matrix for culturing the cells with FGF2. In other aspects, the de-differentiation of fibroblasts is described in the presence of FGF2 with an activated culture surface, further comprising at least one of: histone deacetylate inhibitor, at least one growth factor, culture substrate or combinations thereof. In particular aspects the fibroblasts are cultured according to the methods described herein with FGF2, FGF4, valpronic acid, MATRIGEL® on a glass surface to produce de-differentiated fibroblasts. In certain aspects, the culture conditions further include low oxygen conditions, for example, about 1% to about 10%.

In one aspect, the cells utilized in the methods of the invention, are fibroblasts, for example, adult human dermal fibroblasts. In other aspect of the invention, life span of the fibroblast culture is increased by addition of FGF2. In another aspect, the cells are de-differentiated as evidenced by the presence of a progenitor transcriptional factor.

The cells produced by the de-differentiated methods described herein can be used for tissue/cell therapy in an animal. If appropriate the cells can be derived from the animal in need of therapy. Advantages include avoiding the need for immunosuppressive therapy in autologous cell/tissue transplantation because the cells based therapy from the animal would avoid all forms of immune rejection. Additionally, cells could be cultured as needed in the amounts needed.

As used herein, "de-differentiated" refers to a change in cell phenotype from a differentiated state to a progenitor phenotype. De-differentiation means a transition from a more differentiated state to a less differentiated state, for example a change in morphology to an earlier differentiated state. For example, the measurement of the progenitor phenotype transcription factors or other markers from a differentiated cell or cell culture is obtained, wherein the presence of the progenitor transcription factors or other markers indicates that the cell or cell culture has de-differentiated from a differentiated state that expressed no progenitor transcription factors to one where the progenitor transcription factors or other markers are present. In certain aspects, de-differentiation is observed by the presence of at least one of these transcriptional factors. In other aspects, de-differentiation is observed by increased longevity of the life-span of the cells as compared in the absence of FGF2 and culture conditions.

As used herein "specialized culture conditions" include "culture conditions" for maintaining and proliferation of a de-differentiated cell type. These culture conditions include but are not limited to: growth factors, lower than atmospheric oxygen concentrations, nitrogen concentration, carbon dioxide concentration, cell density, growth medium compositions, cell extracts, specialized culture flasks, activated cell culture surface, growth factor modulators, modulators of growth factor activity and/or stability, extra-cellular matrix compositions, cell culture substrates, histone deacetylate inhibitors, and the like. Further, the culture conditions include a culture medium and in certain aspects, further comprising serum or commercial serum replacement compositions, such as Fetal-CloneIII (Hyclone) and/or ITS (insulin-tranferrin-selenium, Hyclone).

As used herein "low oxygen conditions" refers to an oxygen level below atmospheric (less than 20.9% oxygen) but greater than hypoxic conditions (about 0.5% to about 1%), for example about 5%, about 6%, about 7%, about 8%, about 9%, about 10%, about 11%, about 12%, about 13%, about 14%, about 15%, about 16%, about 17% about 18% and about 19%.

As used herein, "growth factors" include but not limited to: Epidermal Growth Factor, Platelet Derived Growth Factor, Acidic Fibroblast Growth Factor, Transforming Growth Factor alpha, Transforming Growth Factor beta, Keratinocyte Growth Factor, Insulin, Insulin-Like Growth Factor 1 or 2, Tumor Necrosis Factor, FGF4 and combinations thereof.

In certain aspects the concentration of the growth factors are between about 0.1 ng/ml and about 50 µg/ml. For example, the concentration range for insulin is about 0.1 ng/ml to about 50 µg/ml, in some embodiments, 0.1 µg/ml to about 50 µg/ml, in other embodiments, about 10 µg/ml. In one aspect, the concentration range for insulin-like growth factor is about 0.1 ng/ml to about 50 ng/ml. In another aspect, the concentration range for FGF4 is about 0.1 ng/ml to about 50 ng/ml.

As used herein, "progenitor transcription factors" include but are not limited to Oct4, Sox2, nanog, Msx1, Msx2, Stella, Rex 1, Lin28, and Klf4.

As used herein, "tissue and cell-based therapy" are treatments in which the de-differentiated connective cells that have progenitor cell like properties can be administered to an animal and the induced to differentiate into the specific cell type required to repair damaged, destroyed or absent cell tissues. The treatments can be used in animals in need of such treatment.

As used herein, "activated cell culture surface" refers to a culture surface that encourages attachment. Additionally, the surface can play a role in integrin mediated cell signaling to maintain a differentiated state. Examples include, glass surfaces, for example, Thermanox™ (polyethylene teraphalate) and the like.

As used herein, cell culture substrates, for example MATRIGEL®, are substrates that effect cell function and possess the ability to influence cell attachment and proliferation, and growth factor response in cultured cells. (See for example; Ruoslahti, E., *Tumour Biol.*, 17, 117-24 (1996); Raines, E. W. et al., *Ann. N Y Acad. Sci.*, 902, 39-51; discussion 51-2 (2000) and Xu, J. & Clark, R. A., *J. Cell Biol.*, 132, 239-49 (1996)). These substrates comprise proteins (for example, laminin, collagen), growth factors, and other proteins forming extracellular matrix components that effect cell function, attachment and proliferation. The selection of such components can be tested for the desired proliferation outcome as determined by one skilled in the art.

"Therapeutic progenitor cells" as used herein, are de-differentiated cell obtained from any of the methods described herein that are administered to an animal in need thereof for therapy. The therapeutic progenitor cells can then be administered and allowed to de-differentiate to the needed tissue or cells.

Histone deacetylase inhibitors (referred to as HDAC inhibitors, HDI) are a class of compounds that interfere with the function of histone deacetylase. Histone deacetylases (HDACs) mediate changes in nucleosome conformation and are important in the regulation of gene expression. HDACs are involved in cell cycle progression and differentiation, and their deregulation is associated with several cancers. Valproic acid is an example of an HDAC inhibitor.

Basic fibroblast growth factor also known as bFGF or FGF2, is a member of the fibroblast growth factor family. The family includes FGF1, FGF2, FGF3 and FGF4. In some embodiments, modulators of FGFs are also contemplated. For example, heparin sulfate is a known modulator of FGF2 and can be included in the culture conditions to modulate FGF2 activity and/or FGF2 stability.

FGF's, especially FGF2 have been studied widely in their ability to induce cell proliferation and migration, which has prompted many studies of its effect in dermal wound healing. FGF2's are reported to have the ability to alleviate the necessity of feeder cells for maintenance of an undifferentiated cell phenotype in vitro. It had been shown previously that human embryonic stem cells grown in the absence of mouse embryonic feeder cells require FGF2 to remain undifferentiated.

One advantage of the methods described herein is generating cell cultures with increased longevity by use of the growth factor, FGF2 and low oxygen conditions. Such cultures are useful for experimentation, modeling and expansion of primary cells. In one embodiment, a two fold increase is observed over primary cells cultured without these culture conditions. This increase in longevity provides a useful tool to study these cells in experiments and modeling studies. In one aspect of the invention a two fold increase in cell passage is seen. Primary cells typically survive about a 20 to 30 passage rate whereas in the presence of FGF2 and low oxygen conditions passages of 70 times were observed. The therapeutic use of cells with increased life-span include such indication as autologous transplantation for soft tissue injury such as dermal defects (burns), muscle injury, maxillofacial reconstruction.

There is very little information in the literature regarding the specific effect of FGF2 on gene expression in adult human fibroblasts. However, there is data that demonstrates a marked difference in fibroblast migration due to grown factor induction between fetal and adult fibroblasts (Kondo, H. and Y. Yonezawa, "Fetal-Adult Phenotype Transition, in Terms of the Serum Dependency and Growth Factor Requirements, of Human Skin Fibroblast Migration," *Exp Cell Res,* 220(2): 501-4 (1995).). Specifically, fetal and neonatal fibroblasts are more migratory under influence of FGF2, whereas adult fibroblasts are more responsive to PDGF. The lowest FGF2 concentration used in that study was 10 ng/ml which in the protocols described herein halted adult fibroblast proliferation. It is unknown at this time what the effect of this and higher doses might have on gene expression. There may be a morphogenic role after sustained exposure at higher dose or ramping higher doses. The lowest FGF2 concentration used in that study was 10 ng/ml. There is data suggesting a morphogenic role for FGF2 in other cell types, particularly transdifferentiation of retinal pigmented epithelium (Sakaguchi et al., 1997) and regeneration of ganglion cells in chicken retina (Fischer and Reh, 2002).

Interestingly, the presence of FGF2 has been found in the *Xenopus* oocyte as well as both sense and anti-sense mRNA FGF2 transcripts in human eggs (Kimelman, D., J. A. Abraham et al., "The Presence of Fibroblast Growth Factor in the Frog Egg: Its Role as a Natural Mesoderm Inducer," *Science,* 242(4881): 1053-6 (1988); Knee, R. S., S. E. Pitcher et al., "Basic Fibroblast Growth Factor Sense (FGF) and Antisense (gfg) RNA Transcripts are Expressed in Unfertilized Human Oocytes and in Differentiated Adult Tissues," *Biochem Biophys Res Commun,* 205(1): 577-83 (1994); Murphy, P. R. and R. S. Knee, "Identification and Characterization of an Antisense RNA Transcript (gfg) from the Human Basic Fibroblast Growth Factor Gene," *Mol Endocrinol,* 8(7): 852-9 (1994).).

Additionally, data from studies on amphibian limb regeneration implicate FGF1 more so than FGF2 (Zenjari, C., B. Boilly et al., "Nerve-Blastema Interactions Induce Fibroblast Growth Factor-1 Release During Limb Regeneration in Pleurodeles waltl," *Dev Growth Differ,* 39(1): 15-22 (1997).).

The induction of genes that are specific to less differentiated cells is also of interest for applications in wound repair and functional tissue regeneration. The ability to induce less differentiated cells from terminally differentiated cells harvested from a wound site serves the purpose of enhanced tissue repair while retaining site-specific patterning and developmental memory. Development of a delivery vehicle or matrix utilizing FGF2 for more efficient in situ application is also intended.

Initial studies with adult human fibroblasts in *Xenopus* Oocyte Extract (XOE) de-differentiation protocols described herein, showed that these cells were slow growing compared to human neonatal foreskin fibroblasts. The medium was supplemented with FGF2 to increase the proliferation rate. A few attributes of these cultures were observed. First, the onset of increased proliferation was not immediate and took about 3 to about 5 days. Second, the observed cell morphology under FGF2 was altered and the cells are, in general, more spindle shaped with reduced visibility of cytoplasmic fibrous structures using phase contrast microscopy. In short, the cells appear morphologically like neonatal fibroblasts. Also, at the first passage after FGF2 induction, a burst in proliferation rate was observed that then subsides to a more basal level in subsequent passages, yet is overall higher than if cultured without FGF2.

Cells grown in the presence of FGF2 were then used for XOE induced de-differentiation experiments with cells cultured under the same conditions as the XOE treated cells as controls. When the cells were analyzed for certain stem cell markers, a few differences between controls and XOE treated cells for some of the markers was observed. Importantly, in the early transition of cultures grown in the presence of FGF2, control cells were positive by ICC for transcription factors Oct4, Sox2, and Msx1. However, subsequent analysis has failed to show these results by ICC, but western blotting and RT-PCR does show the same positive results for these markers. Eptitope masking in the ICC due to differences in antigen compartmentalization helps explain this discrepancy since the westerns are done on purified proteins. Pretreatment of the cells with 1.5 N HCl for 10 to 40 min unmasks theses nuclear antigens, and Msx-1 is routinely detected in the nucleus of adult human fibroblasts.

Preliminary experiments designed to evaluate a dose response of FGF2 for induction of rapid cell proliferation as well as induction of molecular signatures of less differentiated cells were conducted. The transcription factor, Sox-2, a marker of pluiripotent embryonic stem cells, is induced after culture with as little as 0.5 ng/ml FGF2 for 2 days. Conversely, no Sox-2 expression was detected in concurrent cell cultures without the addition of FGF2. However, this induction of expression was restricted to the cytoplasm and perinuclear accumulation of Sox2 antigen was observed. Upon performing identical experiments on Thermanox™ (Nalge Nunc, Rochester, N.Y.) coverslips with reduced serum to 2%, expression of Msx2, Sox2, and Oct 4 was detected in the nucleus.

Example 1

Methods

Adult human fibroblasts (cell line CRL-2352) derived from connective tissue isolated from tissue derived from a below knee amputation of a 24 year old male were received from American type Tissue Culture Collection (ATCC) (Manassas, Va.) as cryopreserved vials and were stored in liquid nitrogen until use. Cells were thawed at 37 C and added dropwise to 10 ml of basal culture medium (CM-1A, 45% DMEM without L-gln or phenol red (MediaTech, Manassas, Va.) with 4 mM L-Gln (MediaTech), 45% Hams F12 Medium (MediaTech), and 10% Fetalclone III (Hyclone, Logan, Utah)). The cell suspension was centrifuged at 700×g for 5 min, the medium aspirated and the pellet resuspended in fresh CM1A culture medium. Cells were seeded at a density of 0.5×106 in 10 ml of medium in T75 tissue culture flasks (BD Falcon). Cultures were carried out in a 37 C incubator in a humidified environment of 5% $CO_2$, 5% $O_2$, 90% $N_2$. Cells were passaged at routine intervals at approximately 70-90% confluence using Trypsin-EDTA solution (MediaTech) diluted 1:5 in DPBS without Ca2+/Mg2+ (MediaTech). At each passage, cells were counted using a Levy Counting chamber (Hausser Scientific) and the number of population doublings calculated as log 2. For comparative studies, human recombinant FGF2 (either Invitrogen or Chemicon) was supplemented into CM1A at 4 ng/ml (medium designated CM2A) from a 100 µg/ml stock solution in DPBS (MediaTech).

Effect of FGF2 Supplementation on Lifespan In Vitro

Cells were passaged continuously at either 3 or 4 day intervals without interruption until in vitro senescence was reached. Two replicate T25 vessels of cells for each treatment (with or without FGF2) were seeded at each passage with 100,000 cells per vessel. The average number of population doublings (PDs) was calculated at each passage and cumulative PDs plotted versus time (days) in culture (FIG. 1).

Results:

Cells cultured as described above with FGF2 proliferated more rapidly than those without until replicative senescence was reached. On average, an additional 19 population doublings was achieved by addition of FGF2.

Effect of Low $O_2$ (5%) Versus Atmospheric $O_2$ and FGF2 on Proliferation Rate and Lifespan In Vitro Cells were thawed and seeded at equal density into T25 cell culture flasks (BD Falcon) and cultured at 37° C., 5% $CO_2$, balance air (high $O_2$); and 37° C., 5% $CO_2$, 5% $O_2$, 90% $N_2$ (low $O_2$). For each oxygen tension level, cells were also cultured with and without FGF2 (4 ng/ml). Cells were passaged at 3 or 4 day intervals, counted and 100,000 cells re-seeded at each passage. The number of population doublings at each passage was determined and cumulative population doublings compared between low and high $O_2$ treatment groups. In addition, at day 28 of culture, FGF2 was removed from a population of cells and the culture continued to monitor the long term effect of previous culture with FGF2.

Results:

Cells cultured in low $O_2$ with and without FGF2 displayed similar results to those from example one. Cells grown with FGF2 reached senescence after 65 population doublings, while those without FGF2 senesced at 50 PDs. Cells transferred to atmospheric oxygen culture with FGF2 senesced at 49 PDs and cells in atmospheric oxygen without FGF2 senesced at 33 PDs. Data from the distributor of the cell line reported that the cells senesce at 32 PDs. In atmospheric oxygen, regardless of the presence of FGF2, the cells senesced at the same time in culture, although a more rapid growth rate and more cells were obtained with FGF2. These data show an independent effect of both low $O_2$ culture and addition of FGF2 on the in vitro lifespan of the cells, as well as a synergistic effect of FGF2 and low $O_2$.

Effect of Cell Culture Substrate Along with Low $O_2$ (5%) and FGF2 on Expression of Stem Cell Marker Genes.

Adult human fibroblasts (CRL-2352, ATCC) were cultured in conditions of 37° C., 5% $CO_2$, 5% $O_2$ 90% $N_2$ were seeded into 24 well plates (BD Falcon) either without substrate or with 15 mm Thermanox® coverslips (Nalge Nunc) at 5,000 cells per well in medium consisting of DMEM with 4 mM fresh L-glutamine: Ham's F12 medium (50:50) supplemented with 1×TCH serum replacement (Protide Pharmaceuticals), 1×ITS-X (Invritrogen), 2% FetalClone III (Hyclone), and 4 ng/ml FGF2 (Chemicon). After 5 days, the cells were washed with DPBS w/o Ca/Mg (Mediatech) and fixed in methanol (−20° C.) for 10 min, washed with DPBS and stored in DPBS at 4° C. until use. For detection of nuclear antigens (Msx-1, Msx-2, Sox-2, Oct-4 and Nanog), enhanced nuclear membrane permeabilization was performed by incubation with 1.5 N HCl for 20 min, followed by 3 washes (5 min) in PBS. For immuno-cytochemistry, cells were washed with PBS/Tween (PBS, MediaTech with 0.05% Tween-20, Biorad) and blocked for 30 min at RT with PBS containing 0.05% Tween, 5% FBS, and 1% BSA). Primary antibodies (1:200 dilution) were added in blocking solution for 30 min at RT. Cells were washed 4× in PBS/Tween and Alexafluor-568 labeled appropriate secondary antibody diluted 1:1000 in blocking solution added for 30 min. Cells were washed 4× in PBS/Tween and stored in PBS at 4 C until image analysis. Antibodies used were: Msx-1 (SantaCruz, sc-17726), Msx-2 (Santa Cruz, sc-17729), Sox-2 (Abeam, ab15830), Oct4 (Santa Cruz, sc-8630), Nanog (abeam ab21624) FGF receptor-1 (Abgent, AP7636a), FGF Receptor-2 (Abgent, AP7636a), FGF2 (N-terminus, Santa Cruz sc-1390), FGF2 (internal, Santa Cruz sc-79), fibroblast specific protein (FSP, Sigma). Coverslips were removed and mounted onto glass slides in 80% glycerol in PBS containing 0.1% Na-Azide and sealed with nail polish. Cells were visualized using at Olympus IX81 inverted microscope with epi-fluorescence using appropriate filters (Semrock, Inc.) and phase contrast. Images were collected using a 12 bit Hamamatzu CCD camera (Model C4742-80-12AG) and images processes using Slidebook®.

Figure 5:
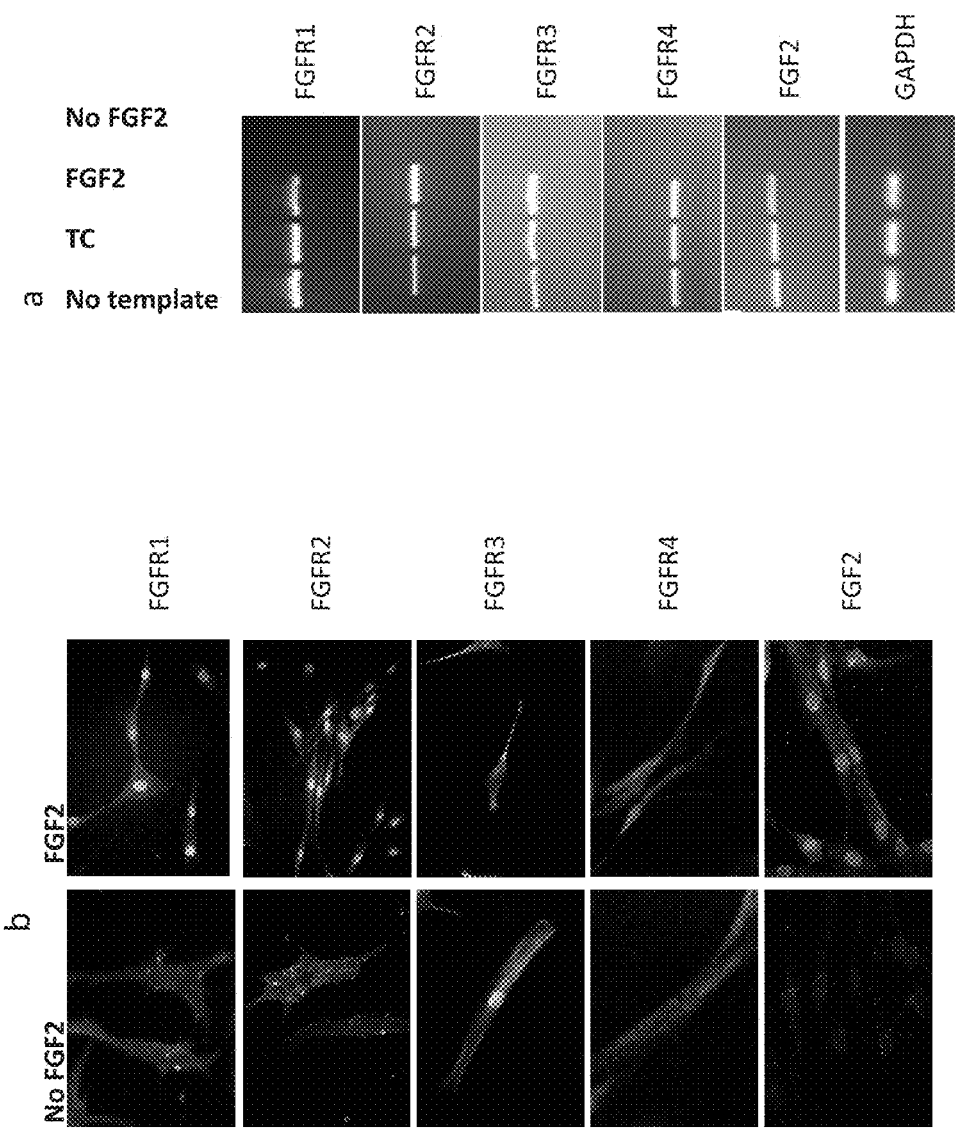
FIG. 5a is a series of gels showing RT-PCR results in control fibroblasts (no FGF2), FGF2 treated fibroblasts, and teratocarcinoma cells (TC). No template control was performed under identical conditions.
FIG. 5b are a series of photographs showing immunofluorescence staining of control and FGF2 treated human adult dermal fibroblasts with antibodies against, FGFR1 (Abgent), FGFR2 (Abgent), FGFR3 (abcam), FGFR4 (Abcam), and FGF2 (Santa Cruz). Secondary antibodies conjugated to Alexafluor 568.

Results:

Cells cultured with low $O_2$, low serum, and FGF2 on tissue culture plastic displayed some cytoplasmic expression of Msx-2, Sox-2, and Oct-4 while those cultured on Thermanox® coverslips displayed nuclear localization of all three transcription factors. Sox-2 and Oct-4 are the hallmark marker genes of human embryonic stem cells. Culture using these conditions also yielded staining for both FGF receptors 1 and 2 in the nucleus as well as on the cell surface. An antibody to the N-terminus of FGF2 detected a great presence of FGF2 on the cell surface while an antibody to an internal peptide detected FGF2 in the nucleus (FIG. 5). This may represent a novel signaling mechanism for FGF2.

Example 2

Methods

Cell Culture

Primary adult human dermal fibroblasts from connective tissue isolated from tissue biopsy from a below knee amputation of a 24 year old male were received from ATCC(CRL-2352) at passage 2. Cells were cultured in medium consisting of DMEM:Ham's F12 (60:40, MediaTech) with 10% Fetalclone III (Hyclone, Logan, Utah). The DMEM (without L-Gln or phenol red) was supplemented with 4 mM fresh L-Gln (MediaTech) prior to use. Cultures were carried out in a 37° C. incubator in a humidified environment of 5% $CO_2$, 5% $O_2$, and 90% $N_2$. The number of population doublings calculated as $log_2$. Cells were seeded at 100,000 cells per T25 flask at each passage (Falcon). When used, human recombinant FGF2 (Chemicon or Protide) and BMP-2 (R&D Systems) was supplemented into medium at 4 ng/ml and 1 ng/ml respectively. Human muscle derived fibroblasts were derived from surplus muscle tissue from the calf flexor muscle used for a surgical knee repair in a 59 year old adult male. Tissue was rinsed in Leibowitz L-15 medium (MediaTech) containing 10 µg/ml gentamicin (Invitrogen) and 2.5 µg/ml fungizone (Hyclone) and minced using a sterile scalpel and digested with 1800 units/ml collagenase Type IV for 1 hour at 37° C. Cell lines were established by culture at 5% $O_2$ from the beginning and working stocks cryopreserved at passage 2.

Immunocytochemistry

Fibroblasts were seeded into 24 well plates (BD Falcon) with 15 mm Thermanox® coverslips (Nunc) or #2 12 mm round glass coverslips (VWR) at 5,000 cells per well in medium consisting of DMEM with 4 mM fresh L-glutamine: Ham's F12 medium (60:40) supplemented with 1×TCH serum replacement (Protide Pharmaceuticals), 1×ITS-X (Invitrogen), 2% FetalClone III (Hyclone) and cultured at 37° C., 5% $CO_2$, 5% $O_2$ and 90% $N_2$. For FGF2 treatments, FGF2 (4 ng/ml) was added to the medium at the time of seeding. After 7 days, the cells were washed with DPBS w/o Ca/Mg (Mediatech) and fixed in methanol (−20° C.) for 10 min, washed with DPBS and stored in DPBS at 4 C until use. Cells were washed with PBS/Tween (PBS, MediaTech with 0.05% Tween-20, Biorad) and blocked for 30 min at RT with PBS containing 0.05% Tween, 5% FBS, and 1% BSA). Primary antibodies (2.5 µg/ml) were added in blocking solution for 30 min at RT. Cells were washed 4× in PBS/Tween and Alexafluor-568 labeled appropriate secondary antibody (4 µg/ml) in blocking solution added for 30 min. Cells were washed 4× in PBS/Tween and stored in PBS at 4° C. until image analysis. Antibodies used were: Oct4 (Abcam ab19857), Sox2 (Abcam, ab15830), Nanog (Abcam, ab21624, FGFR-1 (Abgent, AP7636a), FGFR-2 (Abgent, AP7636a), FGFR3 (Abcam ab10651), FGFR4 (Abcam ab41948), FGF2 (Santa Cruz, sc-1390 and sc-79). Coverslips were removed and mounted onto glass slides in 80% glycerol in PBS containing 0.1% Na-Azide and sealed with nail polish. Cells were visualized using an Olympus IX81 inverted microscope with epi-fluorescence using appropriate filters (Semrock, Inc.) and phase contrast. Images were collected using a 12 bit Hamamatzu CCD camera and processed using Slidebook®.

Western Blotting

Total protein was isolated from subconfluent cultures with RIPA cell lysis buffer (Santa Cruz Biotechnology), supplemented with complete protease inhibitor cocktail (PIC, Santa Cruz Biotechnology) and 1 mM DTT. Lysates were incubated on ice for 30 minutes (vortexing every 10 minutes) and centrifuged at 13,000×g and supernatants stored at −80° C. until use. Protein concentration was determined with Quant-iT protein assay kit (Invitrogen). Equal amounts of protein supernatant and denaturing 2× sample buffer (BioRad Laboratories) were mixed and heated to 95° C. for 3 minutes and separated on 4-20% gradient SDS-PAGE gels and transferred to nitrocellulose membranes (BioRad Laboratories) using Towbins transfer buffer (25 mM Tris, 192 mM glycine, 20% methanol and 0.037% SDS). The membranes were blocked with Tween-Tris buffered saline (TTBS: 25 mM Tris, 137 mM NaCl, 2.7 mM KCl, 0.2% Tween), 5% dry milk (Santa Cruz) and 5% fetal bovine serum. The same buffer was used for primary and secondary antibody incubations. In between antibody incubations, membranes were washed three times with TTBS. Horse radish peroxidase (HRP-conjugated) secondary antibodies were used (Invitrogen). Membranes were incubated in luminol (Santa Cruz Biotechnologies) and luminescence detected using a Kodak 4000 mM Image Station. All images were acquired after 30 second exposure and processed using Kodak imaging software.

Quantitative Reverse Transcription-PCR (qRT-PCR)

RNA was extracted using TRIzol® reagent (Invitrogen) according to the manufacturer's protocol and quantified by spectrophotometry. 2 µg of RNA was subjected to DNase I digestion, followed by a reverse transcription using a QuantiTech® Reverse transcription kit (Qiagen) with a mixture of oligo-dT and random hexamers primers. 50 ng/well of cDNA was used as template in qPCR reactions with oligonucleotides specific for the genes of interest (Table 1 of Supplementary Information). A non-template control (NTC) and an RNA sample without RT for each sample were used to control for potential contaminating DNA. All qPCR reactions were performed in triplicate with the resultant values being combined into an average threshold cycle (CT). The efficiency of qPCR was calculated from the slope of a relative standard curve using GAPDH primers. Relative quantification was determined using a 7500 Real Time PCR system (Applied Biosystems) measuring SYBR green fluorescence (PerfeCTa™ SYBR Green FastMix, Low ROX (Quanta Biosciences)). Fold differences are calculated using the ΔΔCT method with the formula $2^{-\Delta\Delta Ct}$. (Liss, B., "Improved quantitative real-time RT-PCR for expression profiling of individual cells", Nucleic Acids Research 30(17), e89, 2002). Expression profiles for the mRNA transcripts are shown as fold differences in comparison to mRNA levels in control (untreated) fibroblast cells.

Reverse Transcription PCR(RT-PCR)

Total RNA was isolated using Trizol (Invitrogen) following the manufacturer's protocol. Four µg of total RNA was used to perform first strand cDNA synthesis using Superscript (Invitrogen). For RT-PCR, 0.5 µl of the first strand cDNA was used as template. PCR was performed in $Mg^{2+}$ free PCR buffer (TaKara) supplemented with 1.5 mM $MgCl_2$, 200 µM each of dNTPs, 25 pmoles each of forward and reverse primers and 0.5 U of TaKara ExTaq polymerase per reaction. PCR cycling was done as follows: Initial denaturation at 95° C. for 2 minutes followed by 35 cycles of denaturation at 95° C. for 15 seconds; annealing at primer-specific annealing temperature for 1 minute; and extension at 72° C. for 1:30 minutes. Final extension was done at 72° C. for 10 minutes and the samples held at 4° C. until use. Amplification products were resolved on 2% agarose gels containing 0.5 µg/ml ethidium bromide in 1×TAE buffer and photographed using a Kodak 4000 mM Image Station. Primers used are listed in Table 2.

SCID Mouse Injections

Animal studies were done with IACUC approved protocols and in accordance with animal care and use procedures at Worcester Polytechnic Institute, Worcester, Mass. One million of control and one million of FGF2 treated fibroblasts were mixed with 8-12 µm diameter carbon beads in sterile DPBS and injected into the soleus muscle of SCID mice (Charles River. Laboratories). Animals were euthanized 6 weeks after injection, the muscle excised and processed for histology. Tissues were fixed in 4% formaldehyde in DPBS and embedded in paraffin. Sections were stained with H&E and the injection site located by microscopic visualization of the carbon beads.

TABLE 1

Primers used for RT-PCR detection of mRNA for Oct4, Sox2, Nanog, FGFR's 1-4, FGF2, and GAPDH.

| Forward (5') Primer | (SEQ ID NO.) | Reverse (3') Primer | (SEQ ID NO.) |
|---|---|---|---|
| \multicolumn{4}{c}{TABLE 1 RT-PCR primers} | | | |

| Forward (5') Primer | SEQ ID NO. | Reverse (3') Primer | SEQ ID NO. |
|---|---|---|---|
| GTTGATCCTCGGACCTGGCTA | (1) | GGTTGCCTCTCACTCGGTTCT | (2) |
| TGTCTTCTGCTGAGATGCCTCACA | (3) | CCTTCTGCGTCACACCATTGCTAT | (4) |
| CGATCAGATGCAGCCGCAAGTC | (5) | TGTGTAAGGCGAGGTGGTCCGA | (6) |
| GCTTCCTCAGGAACACCAAGA | (7) | TGCAACTTGCTCCAGACACTC | (8) |
| GGAGGAATACCTGGCATTGAC | (9) | CGGCTTCTCTCCAGTATGAAC | (10) |
| GGTTCGGCTTCCTGTCCATGA | (11) | GGTGGCAGCTTGCATTCCTTG | (12) |
| GCCGAGTGGAAACTTTTGTCG | (13) | GCAGCGTGTACTTATCCTTCTT | (14) |
| TGAGTACGGCAGCATCAACCACAC | (15) | CCAGAACGGTCAACCATGCAGAGT | (16) |
| CAATCACACGTACCACCTGGATG | (17) | GTCTGGCTTCTTGGTCGTGTTCT | (18) |
| AGTGGCTCAAGCACGTGGAGGT | (19) | GAGCTCATGGACGCGTTGGACT | (20) |
| GCAATTCCATCGGCCTCTCCTA | (21) | TTGACTTGCCGGAAGAGCCTGA | (22) |
| CTGGCTATGAAGGAAGATGG | (23) | CAGCTCTTAGCAGACATTGG | (24) |
| ATCACCATCTTCCAGGAGCGA | (25) | TTCTCCATGGTGGTGAAGACG | (26) |

TABLE 2
qRT-PCR Primers

| Forward (5') Primer | SEQ ID NO. | Reverse (3') Primer | SEQ ID NO. |
|---|---|---|---|
| AGAGCTACGAGCTGCCTGAC | (27) | GGATGCCACAGGACTCCA | (28) |
| GGCAGCATCAACCACACATA | (29) | TACCCAGGGCCACTGTTTT | (30) |
| GGAGCGTTGCCATTCAAG | (31) | CCTCTACGGGCATGGACTAC | (32) |
| TCCTCGGGAGATGACGAA | (33) | CAGCAGCTTCTTGTCCATCC | (34) |
| AGGCCTCTGAGGAAGTGGA | (35) | ACAGCACAGACGCACAGG | (36) |
| AGCGGCTGTACTGCAAAAAC | (37) | TGCTTGAAGTTGTAGCTTGATGT | (38) |
| GAGTCCACTGGCGTCTTCAC | (39) | TTCACACCCATGACGAACAT | (40) |
| CCATCTTTCTCCACGTTCG | (41) | AGTCGCTTCATGTGGGAGAG | (42) |
| ATGCCTCACACGGAGACTGT | (43) | AAGTGGGTTGTTTGCCTTTG | (44) |
| GAAGCGCAGATCAAAAGGAG | (45) | GCTGATGCTCTGGCAGAAGT | (46) |
| TCGAGAACCGAGTGAGAGG | (47) | GAACCACACTCGGACCACA | (48) |
| CATCGCTGAGCTGAAACAAA | (49) | CTGCTGGACTGTGAGCACTACT | (50) |
| TGATGGAGACGGAGCTGAA | (51) | GGGCTGTTTTCTGGTTGC | (52) |
| GCTGACGTGGAAGATGAGC | (53) | TTGGCCAGGATCTCCTCA | (54) |

TABLE 2

Primers used for qRT-PCR detection and quantification of mRNA's for Oct4, Sox2, Nanog, Rex1, Lin28, Klf4, FGF2, FGFR's 1-4, TERT, and GAPDH. The accession numbers for the Primers of Table 1 and Table 2 are included below under Table 1A and Table 2A.

TABLE 1 A
RT-PCR primers

| Primer Name | SEQ.ID. NO: | Tm | Target Size | Accession number |
|---|---|---|---|---|
| Oct4 | 1, 2 | 60 | 646 | NM_002701 |
| Nanog | 3, 4 | 60 | 387 | NM_024865 |
| Klf4 | 5, 6 | 59 | 365 | NM_004235 |
| TERT | 7, 8 | 58 | 298 | NM_198253 |
| Rex1 | 9, 10 | 58 | 270 | NM_174900 and AF450454 |
| Lin28 | 11, 12 | 57 | 313 | NM_024674 |
| Sox2 | 13.14 | 53 | 154 | NM_003106 |
| FGFR1 | 15, 16 | 58 | 377 | NM_023110; NM_015850, NM_023105, NM_023106, NM_023111 |
| FGFR2 | 17, 18 | 59 | 508 | NM_022970 |
| FGFR3 | 19, 20 | 61 | 442 | NM_000142 and NM_022965 |
| FGFR4 | 21, 22 | 61 | 279 | NM_002011; NM_022963; NM_213647 |
| FGF2 | 23, 24 | 55 | 221 | NM_002006 |
| GAPDH | 25, 26 | 52 | 101 | NM_002046 |

TABLE 2A

| Primer Name | position | Target Size | Accession number |
|---|---|---|---|
| Actin | 27, 28 | 797-907 | 111 | NM_001101 |
| FGFR1 | 29, 30 | variable | 103 | NM_023105, 6, 7, 8, 10, 11 & NM_015850 |
| FGFR2 | 31, 32 | 480-580 | 101 | NM_000141 & NM_022970 |
| FGFR3 | 33, 34 | 644-748 | 105 | NM_000142 & NM_022965 |
| FGFR4 | 34, 36 | variable | 104 | NM_002011, NM_213647 & NM_022963 |
| FGF2 | 37, 38 | 556-665 | 110 | NM_002006 |
| GAPDH | 39, 40 | 391-509 | 119 | NM_002046 |
| KLF4 | 41, 42 | 354-643 | 110 | NM_004235 |
| Nanog | 43, 44 | 349-451 | 103 | NM_024865 |
| Lin28 | 45, 46 | 504-619 | 115 | NM_024674 |
| Oct4 | 47, 48 | 764-888 | 125 | NM_002701 |
| Rex1 | 49, 50 | 222-313 | 92 | NM_174900 |
| Sox2 | 51, 52 | 438-540 | 103 | NM_003601 |
| TERT | 53, 54 | 1579-1686 | 108 | NM_198253 |

Results

When cultured continuously with a rigorously controlled passage schedule, adult human fibroblasts cultured in 5% $O_2$ underwent 50 population doublings (PDs) before reaching senescence compared to 33 for cells cultured in atmospheric oxygen (FIG. 1). Addition of FGF2 to the culture medium with culture in 5% $O_2$, cells underwent 70 PDs. Addition of FGF2 and culture with atmospheric oxygen resulted in 50 PDs. The increase over the expected 33 PDs (according to the cell supplier) was accompanied by change in morphology to smaller cells with a more spindle shape. The FGF2/low oxygen-treated fibroblasts maintained normal karyotype (not shown) and entered replicative senescence as indicated by cessation of further cell division and β-galactosidase staining (not shown). These observations were consistent with those reported previously for fibroblasts cultured in reduced oxygen (Saito, H., et al., *Exp Cell Res.*, 217, 272-9 (1995)), but FGF2 has not been shown to impact cell lifespan. These data indicated both an individual and synergistic role for both reduced oxygen and FGF2 supplementation for increasing cell lifespan, which prompted us to investigate expression of genes related to un-differentiated cells.

Figure 2:
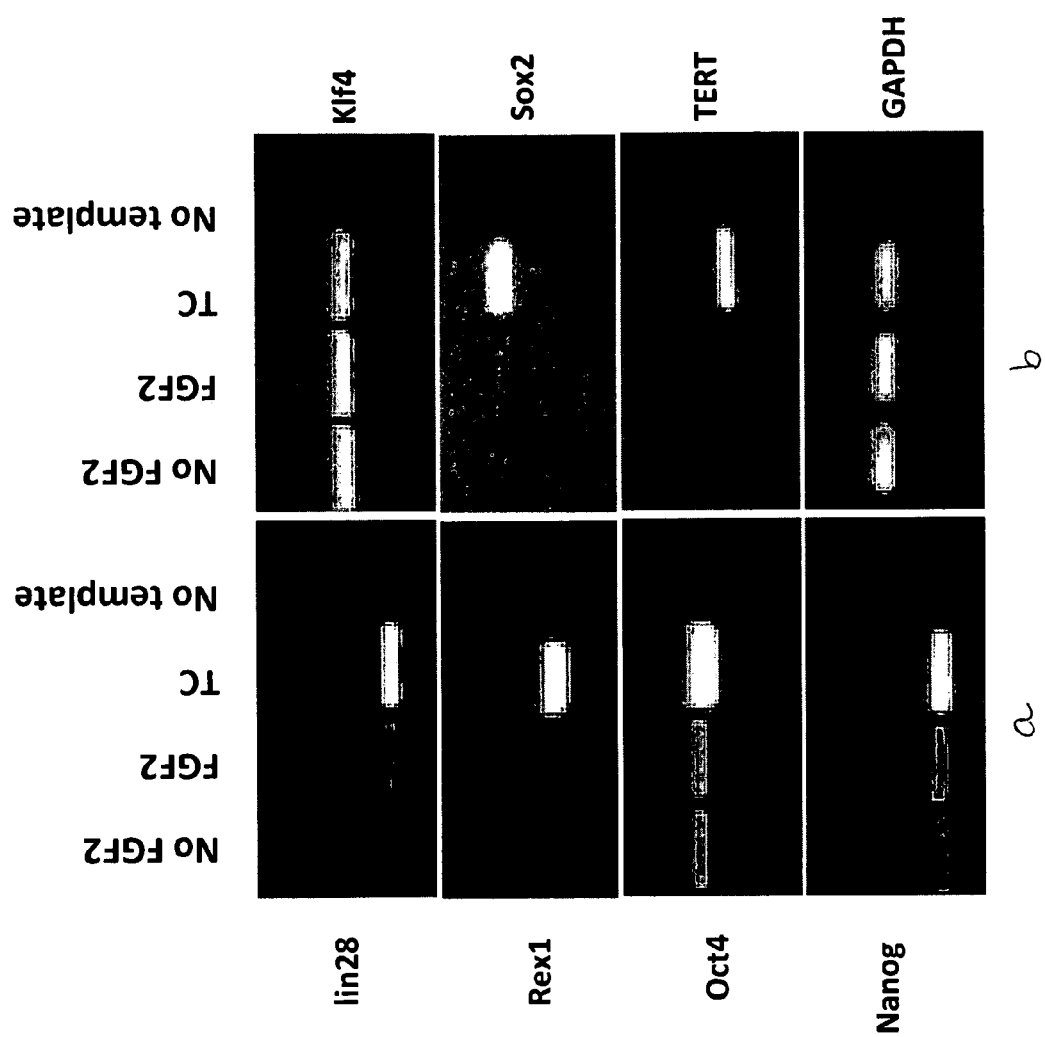
FIG. 2a is a series of gels showing RT-PCR of the same treatments shown in FIG. 1.
FIG. 2b is a series of western blots probed with the same primary antibodies, detected with HRP-conjugated secondary antibodies and visualized with Luminol. C-control, FGF2-FGF2 treated fibroblasts.
Figure 3:
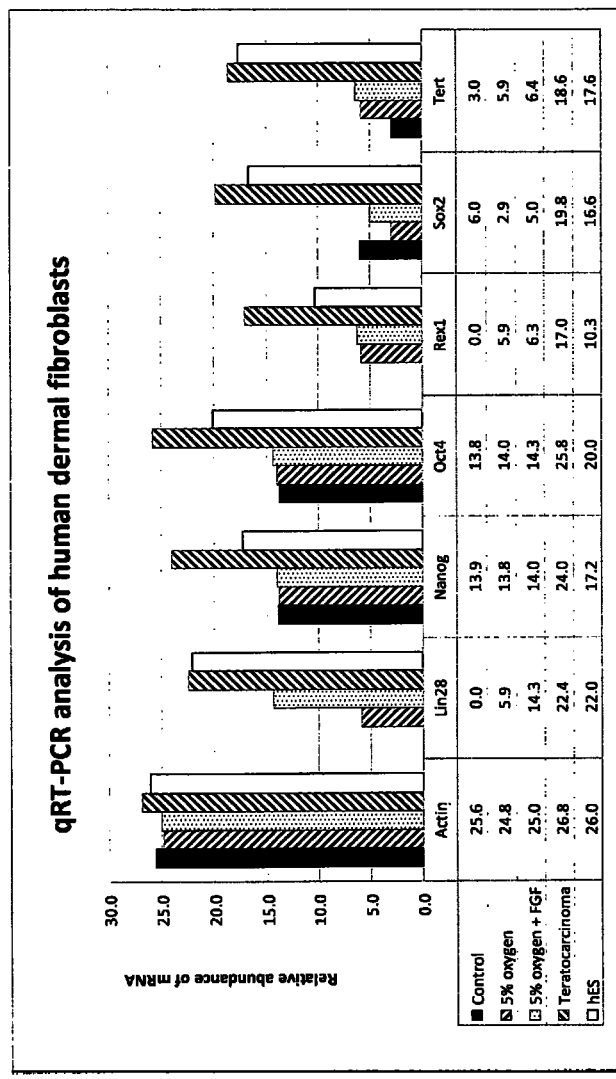
FIG. 3 is a graph showing qRT-PCR results comparing expression level relative to control fibroblasts grown on tissue culture plastic with 10% FBS at atmosperic $O_2$. Treatments were: fibroblasts grown with 10% FCIII at 5% $O_2$, 10% FCIII at 5% $O_2$ with 4 ng/ml FGF2, and human teratocarcinoma cells grown with 10% FCIII at 5% $O_2$ (CRL-2073, ATCC). No template and no reverse transcriptase were performed under identical conditions.

Reverse transcription PCR(RT-PCR) using primers designed to recognize embryonic forms of transcripts for the stem cell genes (Table 1) was performed on day 7 of the initial culture to obtain control baseline values for the cells' transcriptional activity. Contrary to the expected absence of stem cell gene transcripts, RT-PCR amplified detectable amounts of Oct4, Nanog and Klf4 mRNA in fibroblasts grown under 5% oxygen. Transcription of these genes increased when cultures were supplemented with FGF2 and the amplified transcripts were of the same size as those present in human teratocarcinoma cell controls (FIG. 2). Other stem cell genes Sox2, Rex1 and Lin28 and showed significant transcriptional dependence on FGF2 (FIG. 2). Neither lowered oxygen nor FGF2 supplementation had an obvious effect on expression of Oct4, Nanog, Klf4 or hTERT, when compared to GAPDH controls (FIG. 2). A Western blot analysis was performed to evaluate the potential significance of the presence of stem gene transcripts in fibroblasts and to determine whether the messages were being translated. The appearance of Oct4, Sox2 and Nanog was not a consequence of transcriptional upregulation as the levels of mRNA for both remained unchanged in control untreated fibroblasts and did not increase after treatment (FIG. 2b). Quantitative real time PCR (qRT-PCR) was employed to quantify these observations and the analysis confirmed the RT-PCR data (FIG. 3). Reduced oxygen culture resulted in an increase in Rex1 and TERT mRNA which was not further affected by FGF2 (FIG. 3). Addition of FGF2 further increased mRNA levels for Lin28.

Figure 4:
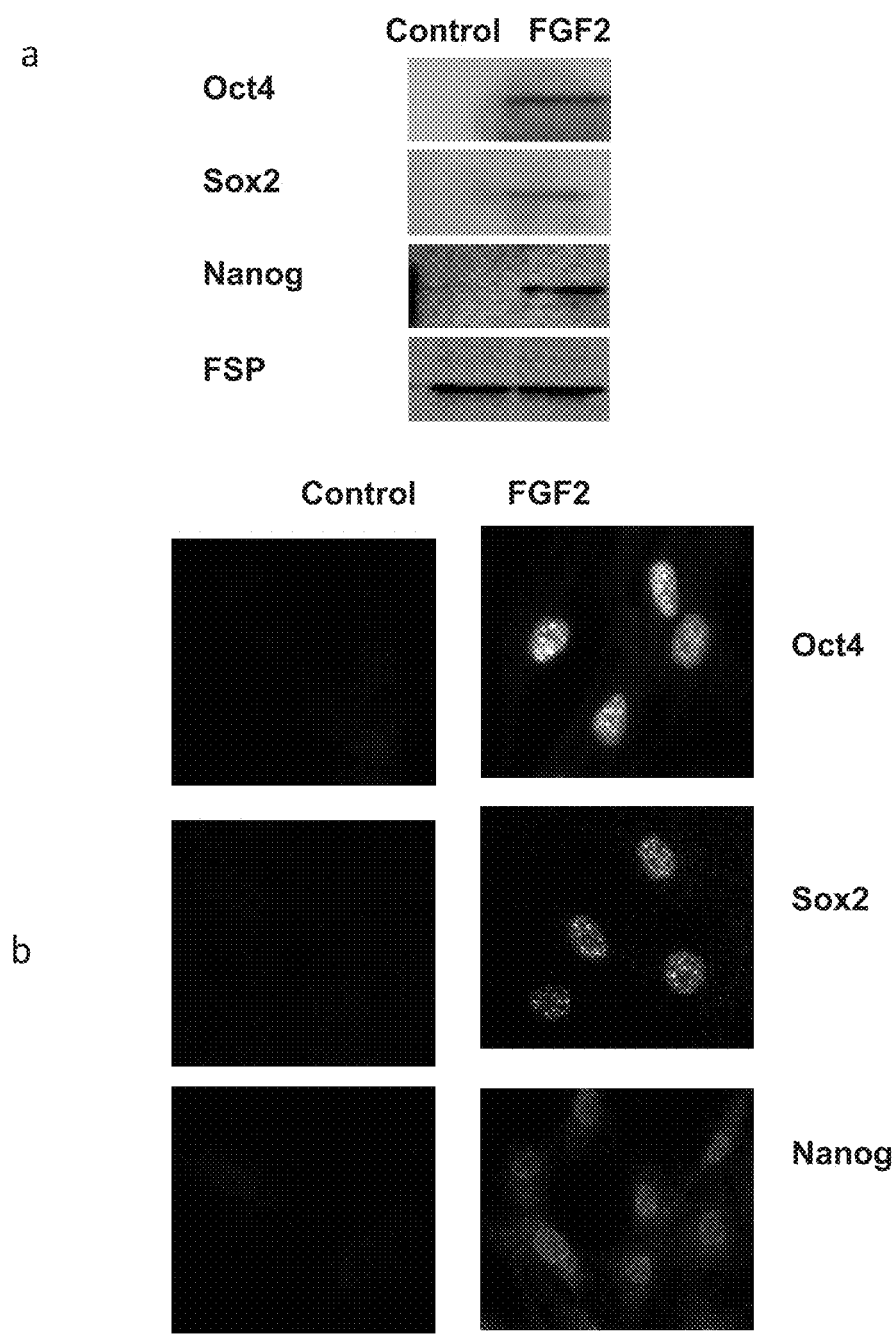
FIG. 4a is a series of western blots showing the effect of FGF2 on Oct4, Sox2, and Nanog expression.
FIG. 4b are photographs of cells stained by immunocytochemistry and shows the effect of FGF2 on translation and nuclear translocation of Oct4, Sox2 and Nanog.

FIG. 4a is a western blot showing the effect of FGF2 on Oct4, Sox2, and Nanog expression. FIG. 4b are photographs of cells stained by immunocytochemistry and shows the effect of FGF2 on translation and nuclear translocation of Oct4, Sox2 and Nanog.

The unexpected detection of apparent translation and nuclear translocation of Oct4, Sox2 and Nanog in fibroblasts due to FGF2 prompted further evaluation of the expression of FGF2 itself and its receptors in cells cultured under these conditions. Supplementation of FGF2 had no significant effect on transcription of FGF receptors or FGF2 itself regardless of the culture conditions (FIG. 5a). However, immunocytochemistry showed that in cells supplemented with FGF2, FGF2 itself and both, FGFR1 and FGFR2 translocated to the nucleus, while FGFR3 was detected in the nucleus in the absence of FGF2 (FIG. 5b). FGF2 addition had no effect on FGFR4 localization (FIG. 5b). Nuclear translocation of FGF2 receptors has been observed in 3T3 cells (Maher, P. A., *J. Cell Biol.*, 134, 529-36 (1996)). and mammary epithelial cells (Bryant, D. M. & Stow, J. L., *Traffic*, 6, 947-54 (2005). and has been associated with FGF2 mitogenic activity, which may act through a number of FGFR isoforms. These changes in FGFR and FGF2 localization did not appear to coincide with a specific pattern of changes at the mRNA level. Nuclear localization of FGF2 and its two receptors in FGF2 treated cells raises the possibility for altered FGF2/FGFR nuclear signaling due to interactions with the cell substrate. Both FGFR1 and 2 have been associated with FGF2 mediated maintenance of pluripotency in hES cells (Babaie, Y., R. Herwig, et al. (2007). "Analysis of Oct4-dependent transcriptional networks regulating self-renewal and pluripotency in human embryonic stem cells." *Stem Cells*, 25(2): 500-10; Greber, B., H. Lehrach, et al. (2007). "Silencing of core transcription factors in human EC cells highlights the importance of autocrine FGF signaling for self-renewal." *BMC Dev Biol.*, 7: 46.) Recently, FGF2 has been shown to be involved in remodeling of the chromatin in rat cortical neuronal progenitor cells by methylation of histone H3K4me3 and repression of methylation of H3K9 (Song, M. R. & Ghosh, A., *Nat. Neurosci.*, 7, 229-35 (2004)). Both of these post-translational histone H3 modifications have been traditionally associated with transcriptionally active chromatin (Kimura, H., Tada, M., Nakatsuji, N. & Tada, T., Mol Cell Biol 24, 5710-20 (2004)).

The effect of valproic acid on FGF2 de-differentiation was also studied. CRL-2352 (ATCC) cells (2000 cells per well in 24-well plates containing sterile 12 mm glass coverslips) were cultured in medium consisting of DMEM:Ham's F12 (60:40, MediaTech) with 10% Fetalclone III (Hyclone, Logan, Utah) and 4 ng/ml FGF2, with and without 1.0 µM valproic acid, in parallel cultures. Cultures were carried out in a 37° C. incubator in a humidified environment of 5% $CO_2$, 5% $O_2$, and 90% $N_2$ for 6 days with medium changed at day 3. Cells were washed with DPBS and fixed with −20° C. methanol for 10 min, washed with PBS and processed for immunocytochemistry. Cells cultured with valproic acid displayed increased nuclear staining for Nanog.

Figure 6:
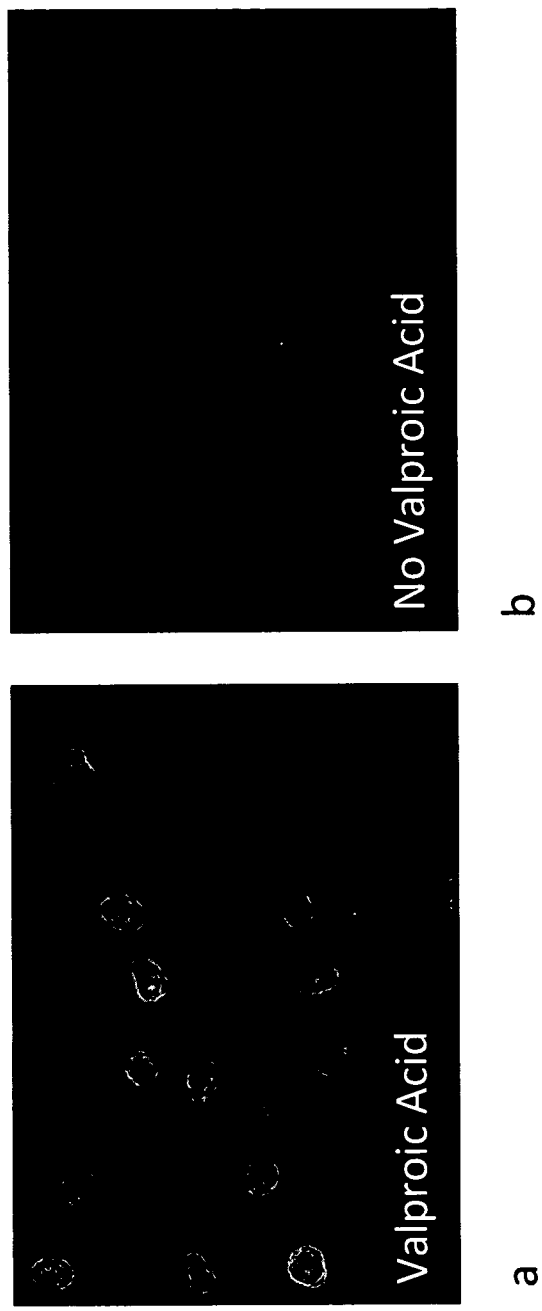
FIGS. 6a & 6b are slides showing the effect of vaproic acid on expression of Nanog with FGF2 (4 ng/ml) of adult human fibroblasts. Images were captured using identical capture settings and processed using Slidebook®.

FIG. 6 demonstrates the effect of valproic acid with FGF2 and glass substrate on activation and nuclear expression of pluripotent genes.

Also, BMP signaling has been shown to antagonize FGF2 signaling in maintaining the pluripotent state of human ES cells (Xu, R. H. et al., *Cell Stem Cell* 3, 196-206 (2008)) While FGF2 has not been implicated previously in transcriptional activation of Oct4 or Sox2, it has been determined that the maintenance of expression of these genes and cell pluripotency is dependent on FGF2. The proposed action of FGF2 involves induction of members of TGF-β pathway; TGF-β ligands maintain expression of Oct4, Sox2, and Nanog which in turn activate expression of endogenous FGF2 that completes this regulatory loop Greber, B. et al., *BMC Dev Biol.*, 7: 46 (2007)).

Figure 7:
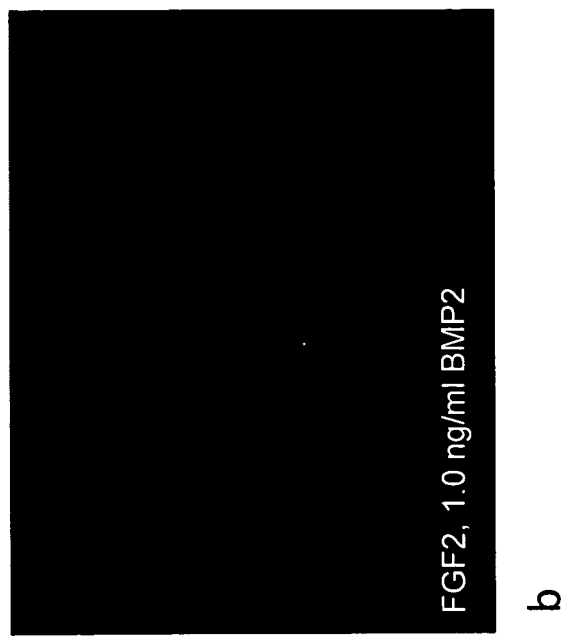
FIGS. 7a & 7b are slides showing the inhibitory effect of BMP-2 on expression of Oct4 with FGF2 of adult human fibroblasts.
Figure 7:
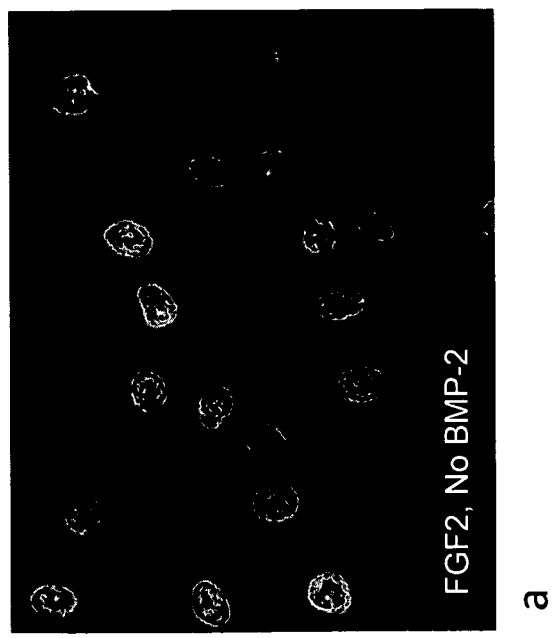

FIGS. 7a and 7b show the inhibitory effect of BMP-2 on Oct2 expression.

The alteration of cell fate can depend not only on induction of new transcription, but on post-transcriptional regulation as well. The absence of tumor formation after injection into SCID mice indicates that despite stem cell gene expression, their translation and appropriate nuclear localization after 7 days of culture, that these cells have not acquired a pluripotent phenotype. Events that lie downstream of Oct4, Sox2 and Nanog and may be critically important for acquisition and maintenance of pluripotency may require extended culture of cells under appropriated conditions. Since only up to 30% of cells demonstrated stem-like nuclear localization of the transcription factors, absence of tumor formation may have been due to insufficient numbers of Oct4/Sox2 positive cells injected. The ability of lowered oxygen together with FGF2 to induce expression of stem cell genes in adult human fibroblasts without hTERT protein expression and with a significantly increased replication potential suggests that sufficient numbers of cells could be produced for therapeutic applications.

In addition, mechanisms regulating translation and post-translational modifications can be critically important in induction of a stem cell phenotype. This suggests that there is a sub-population of fibroblasts capable of responding to FGF2 at the translational or signaling level. Basic fibroblast growth factor (FGF2) has been shown to regulate human ES cell self-renewal. It is also a potent mitogen and morphogen for a variety of cell types (reviewed in Ornitz and Itoh, *Genome Biol*, 2, REVIEWS 3005 (2001)). Interestingly, FGF2 has also been shown to initiate regeneration in the eye and reprogram primordial germ cells to pluripotency (Hayashi, T. et al., *Mech Dev.*, 121, 519-26 (2004) and Durcova-Hills, G., *Stem Cells* 24: 1441-9 (2006)).

The mechanism of induction of key regulatory genes involved in pluripotency by non-transgenic methods to create truly pluripotent cells will require further investigation. The published studies on transgene induced pluripotency in fibroblasts show that forced expression of exogenous pluripotency genes is required for at least 30 days prior to detection of phenotypic changes in the cells followed by amplification of colonies of cells with truly pluripotent properties. The long term stability of this phenotype will likely involve introduction of extra cellular components and specialized media formulations similar to those employed for derivation and in vitro maintenance of hESCs and IPS cells. Utilizing the methods described herein, it can be possible to induce differentiated cells to the pluripotent state by modifying the in vitro culture conditions.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing a cell population that expresses Oct4, comprising the steps of:
   culturing mammalian fibroblast cells in a medium that comprises between 2 ng/ml and 9 ng/ml of FGF2 and between 1% and 10% oxygen, thereby producing a cell population that expresses Oct4,
   wherein the cell population expresses increased amounts of Oct4 compared to mammalian fibroblasts cultured in a medium that comprises between 2 ng/ml and 9 ng/ml of FGF2 and atmospheric oxygen.

2. The method of claim 1, wherein the FGF2 is recombinant human FGF2.

3. The method of claim 1, wherein the mammalian fibroblast cells are human.

4. The method of claim 1, wherein the low oxygen conditions comprises about 5.0% oxygen.

5. The method of claim 1, wherein the medium further comprises other growth factors.

6. The method of claim 5, wherein the growth factors are selected from the group consisting of: Epidermal Growth Factor, Platelet Derived Growth Factor, Acidic Fibroblast Growth Factor, Transforming Growth Factor alpha, Transforming Growth Factor beta, Keratinocyte Growth Factor, Insulin, Insulin-Like Growth Factor 1 or 2, Tumor Necrosis Factor, FGF4, and combinations thereof.

7. The method of claim 5, wherein the growth factor is insulin or insulin like growth factor 1 or 2.

8. The method of claim 1, wherein the culturing conditions include culturing on an activated cell culture surface.

9. The method of claim 8, wherein the cell culture surface is glass.

10. The method of claim 1, further comprising heparan sulfate.

11. The method of claim 1, further comprising a histone deacetylase inhibitor.

12. The method of claim 1, further comprising a culture substrate.

13. The method of claim 12, wherein the substrate includes one or more extracellular matrix proteins.

14. The method of claim 1, wherein the medium comprises approximately 4 ng/ml of FGF2.

15. The method of claim 11, wherein the histone deacetylase inhibitor is valproic acid.

16. The method of claim 1, wherein the fibroblasts reach senescence after 60 days and before 75 days in culture.

17. The method of claim 1, wherein expanding the fibroblast cells to a resultant cell population occurs by permitting more than 50 doublings and less than or equal to 70 doublings.

* * * * *